United States Patent [19]

Jones, Jr. et al.

[11] Patent Number: 5,724,986
[45] Date of Patent: Mar. 10, 1998

[54] CASING AND SPIROMETER FOR METERED DOSE INHALER

[75] Inventors: William C. Jones, Jr.; Scott E. Jones, both of Chicago, Ill.

[73] Assignee: Jones Medical Instrument Co., Oakbrook, Ill.

[21] Appl. No.: 554,552

[22] Filed: Nov. 6, 1995

[51] Int. Cl.$^6$ ............................................. A61M 15/00
[52] U.S. Cl. ...................... 128/725; 604/45; 128/200.14; 128/201.26; 128/201.21
[58] Field of Search ........................ 128/725, 200.14, 128/200.19, 200.21, 200.26, 201.26, 201.28, 203.23; 604/45

[56] References Cited

U.S. PATENT DOCUMENTS

| | | | |
|---|---|---|---|
| D. 335,343 | 5/1993 | Jones et al. | D24/110 |
| 4,291,688 | 9/1981 | Kistler | 128/200.23 |
| 4,604,847 | 8/1986 | Moulding, Jr. et al. | 53/75 |
| 4,942,544 | 7/1990 | McIntosh et al. | 364/569 |
| 4,984,158 | 1/1991 | Hillsman | 364/413.04 |
| 4,991,591 | 2/1991 | Jones et al. | 128/719 |
| 5,076,093 | 12/1991 | Jones, Jr. et al. | 73/3 |
| 5,170,798 | 12/1992 | Riker | 128/725 |
| 5,363,842 | 11/1994 | Mishelevich et al. | 128/200.14 |
| 5,364,838 | 11/1994 | Rubsamen | 514/3 |
| 5,404,871 | 4/1995 | Goodman et al. | 128/200.14 |
| 5,408,994 | 4/1995 | Wass et al. | 128/200.14 X |
| 5,540,336 | 7/1996 | Rubsamen et al. | 364/571.01 |

FOREIGN PATENT DOCUMENTS

| | | |
|---|---|---|
| 0 387 222 | 3/1990 | European Pat. Off. |
| 0 667 168 | 2/1994 | European Pat. Off. |
| WO 92/15353 | 3/1992 | WIPO |
| WO 93/12823 | 12/1992 | WIPO |
| WO 94/16757 | 1/1994 | WIPO |

OTHER PUBLICATIONS

"How should a pressurized β–adrenergic bronchodilator be inhaled", *Eur J. Resp Dis*, (1981) 62, 3–21.

"Introduction to Motorola Pressure Sensors," *Motorola Sensor Device Data*, pp. 1–4,1–5, 6–11 and 6–12.

*Primary Examiner*—John P. Lacyk
*Assistant Examiner*—Stephen Huang
*Attorney, Agent, or Firm*—Tilton, Fallon, Lungmus & Chestnut

[57] ABSTRACT

An apparatus for dispensing a metered amount of aerosolized medication and/or for measuring breathing function includes a casing that defines a cavity, a first or discharge opening from which a subject inhales from the cavity or exhales into the cavity, a second or air opening through which air enters the cavity, and a third opening in fluid communication with the cavity between the first and second openings. The casing also defines an open pocket for receiving a pressurized canister and a fourth or medication opening through which the contents of the canister discharge into the cavity of the casing. A pressure transducer in fluid communication with the third opening senses the pressure of breath moving through the cavity. Alternatively, a fan and photocell assembly may replace the pressure transducer and sense the flow of gas through the cavity.

22 Claims, 5 Drawing Sheets

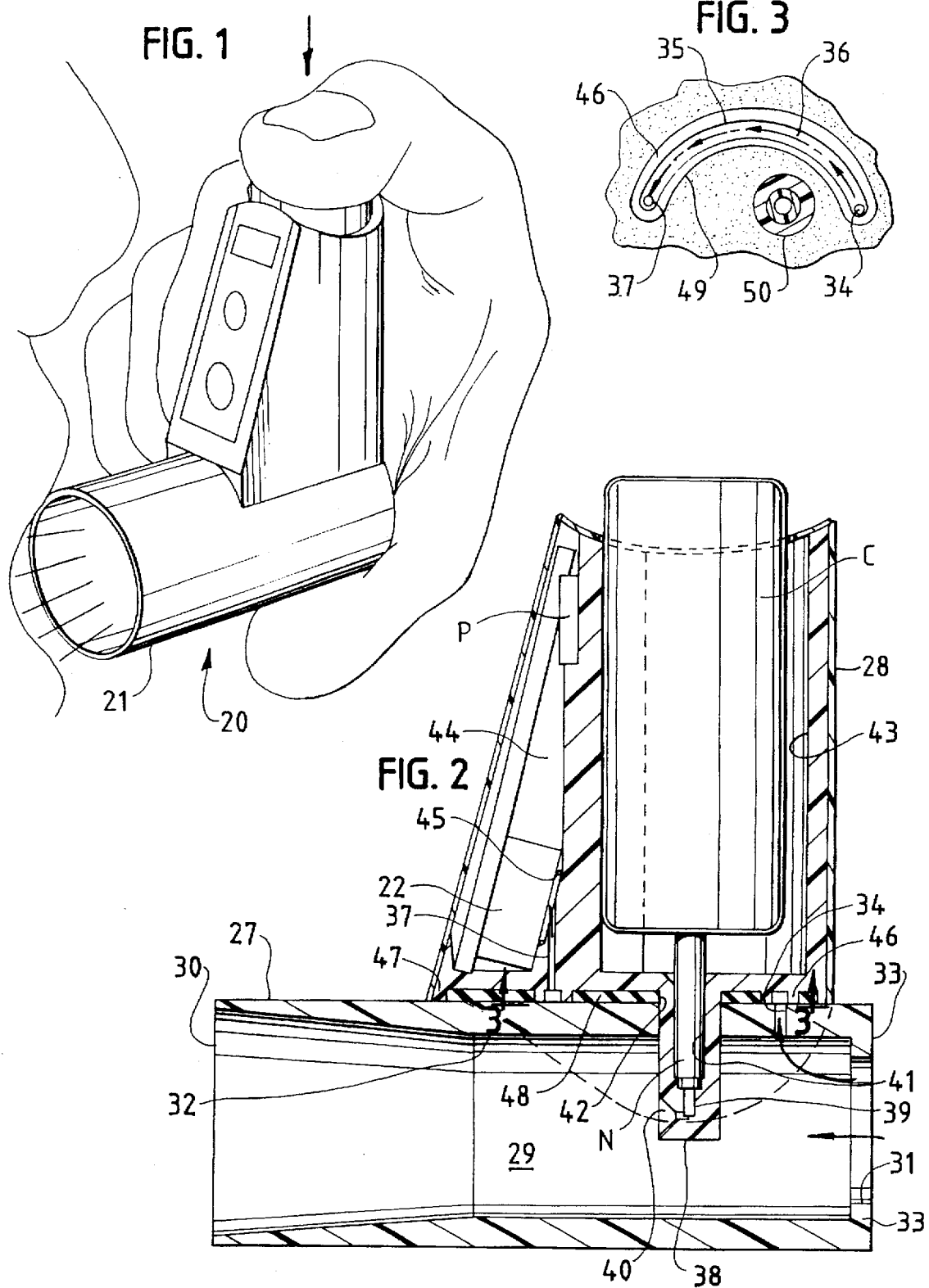

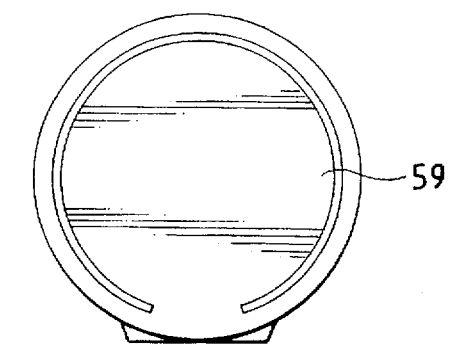
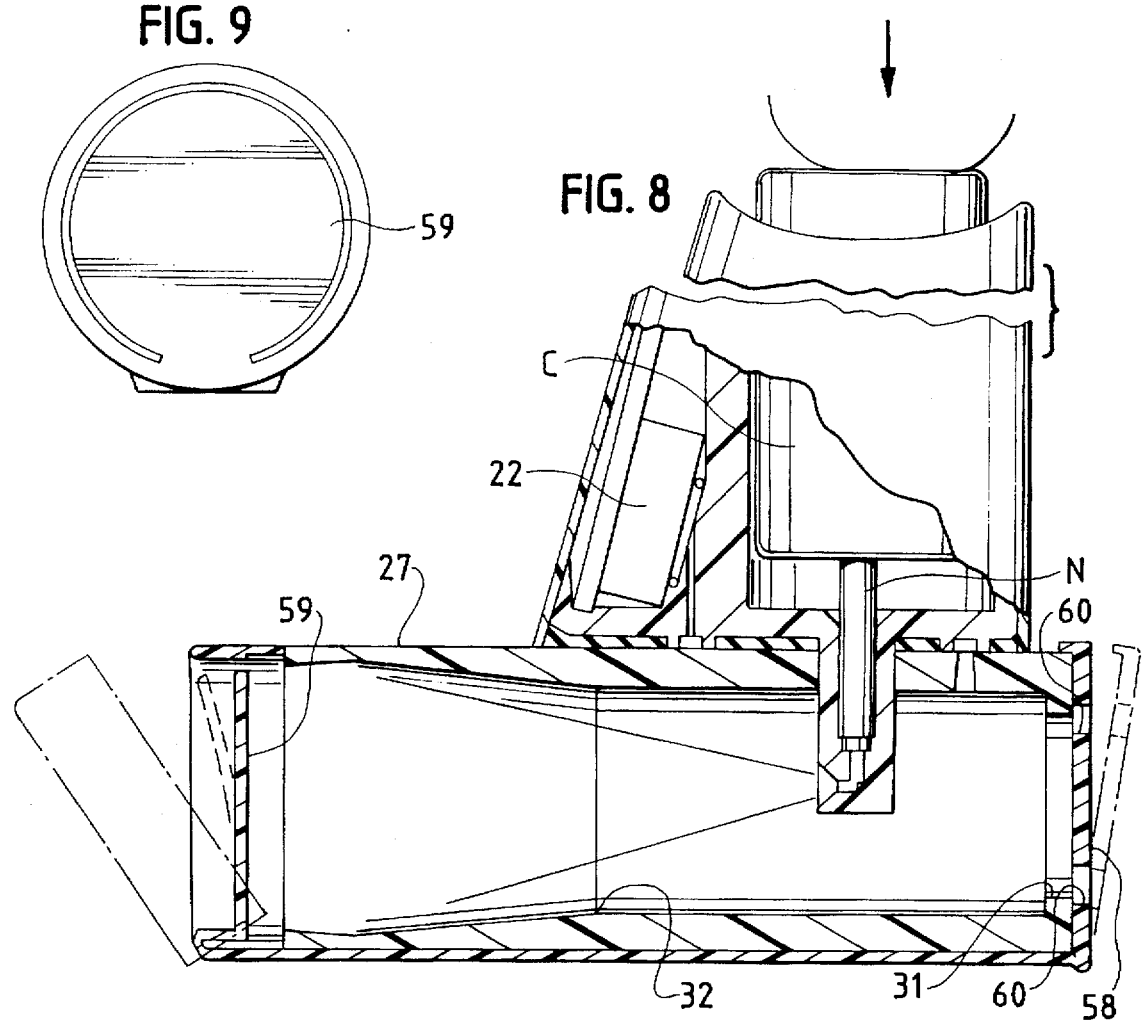
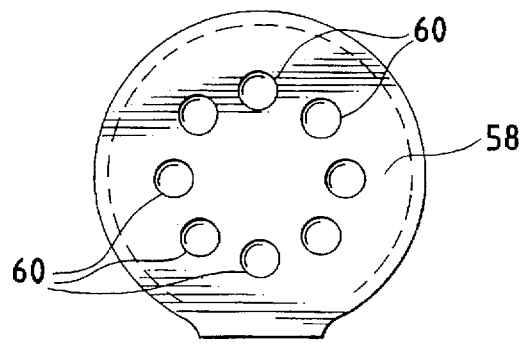

CASING AND SPIROMETER FOR METERED DOSE INHALER

BACKGROUND OF THE INVENTION

1. Field of the Invention

The present invention generally relates to a dispenser for aerosolized medication and more particularly to a dispenser that provides a metered amount of aerosolized medication and measures the pulmonary function of a subject to monitor this function and to determine the optimum conditions for administering the medication, based on: 1) routine (date and time) scheduling of medication, as prescribed by a physician; 2) precise administration of medication based on flowrate, volume, and timing, as outlined by the pharmaceutical manufacturer; and 3) the need to alleviate symptoms, as perceived by the patient.

2. Description Of The Prior Art

A metered dose inhaler is a small pocket-sized device that generally comprises two components: (1) a pressurized canister filled with a propellant (aerosol) and medication for opening constricted airways in subjects with asthma, chronic bronchitis, emphysema or other such diseases, and (2) a casing that houses the canister and facilitates the delivery of medication into a subject's lungs. The subject dispenses the medication by inserting a mouthpiece of the casing into his or her mouth and pressing the top of the canister while inhaling.

A subject may use the metered dose inhaler separately or in association with a "spacer". Spacers are known devices designed to extend the discharge tube of an inhaler and allow large droplets in the aerosolized medication to settle to their bottoms.

Spirometers are devices that measure the breathing volume and the breathing rate of human subjects. They are the most accurate means for diagnosing and monitoring pulmonary function. But, they are not pocket-sized devices. In addition, they include a multiplicity of close tolerance components that make them susceptible to malfunctions and expensive to produce.

Other devices that allow subjects to monitor their pulmonary function include mechanical peak flow meters. These flow meters, however, are inaccurate. They do not effectively detect clinically significant function changes in asthmatics, for example. In addition, they can only measure peak expiratory flow (PEF) and not the forced expiratory volume in one second (FEV1, i.e., the volume of air exhaled during the first second, a widely accepted measure of pulmonary function).

Metered dose inhalers are the primary means of drug delivery in those patients with breathing disorders; and the prior art includes a wide variety of such inhalers. However, the prior art does not include inhalers with any means (e.g., spirometers) for monitoring pulmonary function and measuring the optimum conditions for delivering the medication.

The casing and spirometer of the present invention provides a construction that measures the pulmonary function of the subject and dispenses the aerosolized medication to a subject based on the optimum conditions for administering the medication. This construction eliminates the need for a subject to purchase, carry, and knowledgeably utilize separate metered dose inhalers, peak flow meters, and spacer devices. It measures the PEF and FEV1 of the subject precisely and reliably, while facilitating use of the proper techniques for administering the medication.

SUMMARY OF THE INVENTION

In accordance with one embodiment of the present invention, an apparatus for dispensing a metered amount of aerosolized medication and/or for measuring pulmonary function includes a casing that defines an open cavity through which a subject breathes. The casing also defines a first, discharge opening through which the medication discharges and the subject inhales or exhales; a second, air opening through which air enters and exits the cavity; and a third opening in fluid communication with the cavity between the first and second openings. The casing further defines an open pocket for receiving a pressurized canister containing medication and a fourth, medication opening through which the contents of the canister discharge into the cavity. A pressure transducer in fluid communication with the third opening senses the pressure of breath moving through the cavity.

The pressure transducer measures the back pressure of the breath which moves through the cavity between the first and second openings. In the embodiment described above, a difference in the cross-sectional area between the first and second openings produces the back pressure. (The first opening has a greater cross-sectional area than the second opening.) A modification of this embodiment may include first and second openings with the same cross-sectional area but with screens, grids, or filter paper over the second opening to create the back pressure. Another modification may include a fan disposed in the cavity and a photocell assembly. This modification senses the flow of gas through the cavity. Yet another modification comprises a valve member for closing the first opening to allow droplets in the medication to settle in the cavity before the subject inhales the otherwise aerosolized medication. This valve member opens under the force of the inhaled breath of the subject to allow the aerosolized medication to flow into the subject.

BRIEF DESCRIPTION OF THE DRAWINGS

For a more complete understanding of this invention, one should now refer to the embodiment illustrated in greater detail in the accompanying drawings and described below by way of an example of the invention. In the drawings:

FIG. 1 is a perspective view of an embodiment of the casing and spirometer apparatus of the present invention;

FIG. 2 is a sectional view taken along a longitudinal axis of the mouthpiece portion of the casing;

FIG. 3 is a sectional view taken along line 3—3 in FIG. 2;

FIG. 4 is an exploded perspective view of the casing and spirometer apparatus;

FIG. 5 is a schematic of the sensing, display and control components of the casing and spirometer apparatus;

FIG. 6 is the sectional view of FIG. 2, showing a first modification of the embodiment of FIGS. 1–5;

FIG. 7 is the sectional view of FIG. 2, showing a second modification of the embodiment of FIGS. 1–5;

FIG. 8 is the sectional view of FIG. 2, showing a third modification of the embodiment of FIGS. 1–5;

FIG. 9 is a front elevation view of the mouthpiece portion of the casing shown in FIG. 8; and FIG. 10 is a back elevation view of the mouthpiece portion of the casing shown in FIG. 8.

While the following disclosure describes the invention in connection with one embodiment and a number of modifications of that embodiment, one should understand that the invention is not limited to this embodiment and modifications. Furthermore, one should understand that the drawings are not to scale and that graphic symbols, diagrammatic representatives, and fragmentary views, in part, may illustrate the embodiment and modifications. In certain instances, the disclosure may not include details which are not necessary for an understanding of the present invention such as conventional details of fabrication and assembly.

DETAILED DESCRIPTION OF THE DRAWINGS

Figure 4:
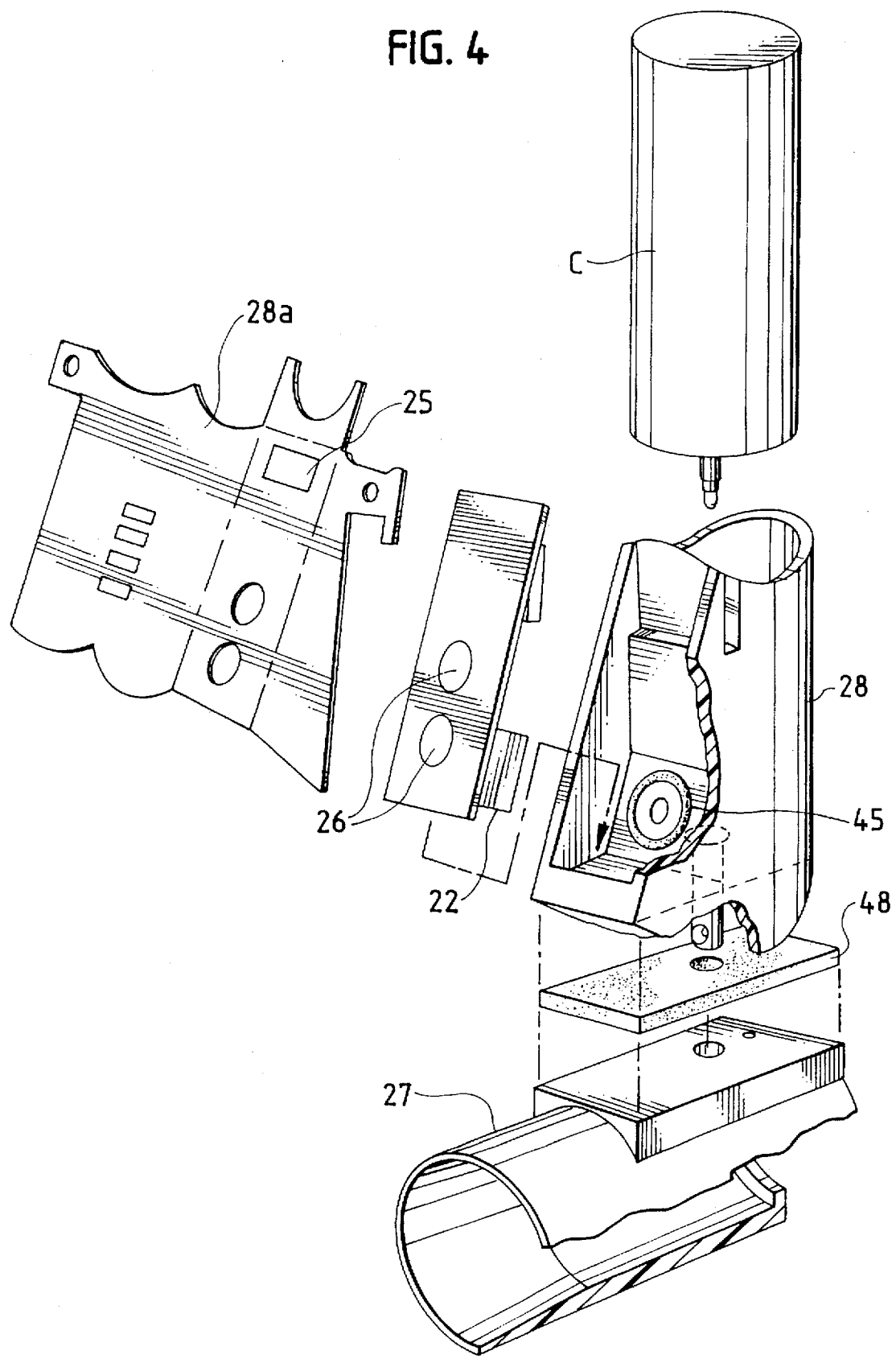

Turning now to the drawings, FIGS. 1 through 5 show an embodiment of the casing and spirometer apparatus of the present invention at 20. The apparatus generally includes a pocket-sized casing 21 that a user may easily hold in the palm of his or her hand; an electronic pressure transducer 22 (see FIG. 2) which measures the back pressure of the breath moving through the casing 21; and computer controls 23 (see FIG. 5), including a central processing unit 24, an LCD display 25, and switches 26 connected together electrically.

The casing 21 includes a tube segment 27 and a canister segment 28 fixedly secured (e.g., sonically welded) together to form the casing. The two segments are made out of plastic or any other material of high strength and rigidity. The tube segment 27 is an elongate, round tube that defines a cavity or central bore 29, a first opening 30 disposed at one end of the cavity 29 and a second opening 31 disposed at an opposite end of the cavity. The first opening 30 is a discharge opening through which a subject receives the aerosolized medication provided by the apparatus. The second opening 31 is an air opening through which ambient air enters the cavity 29 when the subject inhales through the cavity and through which air discharges from the cavity when the subject exhales into the cavity 29.

The diameter of the bore 29 decreases at a constant rate between the opening 30 and a point 32 (See FIG. 2) to minimize air resonance artifacts. From the point 32 to the opening 31, the bore has a constant diameter to facilitate laminar flow. At the opening 31, the tube segment 27 includes a flange portion 33 that reduces the diameter of the bore to the diameter of the opening 31. This constriction in the flow path of breath moving through the casing 21 provides the back pressure that the pressure transducer 22 senses.

The tube segment 27 also defines a bore 34 through which the pressure transducer 22 senses the back pressure in the bore 29. This bore 34 is part of a third opening 35 that also includes a passageway 36 (See FIG. 3) disposed between the tube segment 27 and the canister segment 28 and a bore 37 defined by the canister segment 28. The volume of this opening 35 is sufficiently small to maximize the pressure sensitivity of the transducer 22.

The canister segment 28 includes a protuberance 38 that defines a fourth or medication opening 39 for the casing 21. This opening 39 includes a conical outlet portion 40 through which aerosolized medication sprays out into the bore or cavity 29 and an enlarged inlet portion 41 that receives a nozzle N of a pressurized, medication canister C. The protuberance 38 extends into the bore 29 through a suitably sized opening 42. The distal end of the protuberance 38 extends to a point proximate the middle of the bore 29.

The canister segment 28 also defines a pocket 43 that receives the canister C and a pocket 44 that receives the transducer 22, a power source P for the computer controls 23 and a resilient O-ring 45. (The O-ring 45 lies around the bore 37 between a wall portion circumjacent the bore 37 and the transducer 22 to prevent escape of the fluid flowing through the bore 37 and onto the transducer 22.) The pocket 43 is a round, elongate bore, open at one end for receiving the canister C. It lies generally perpendicularly to the bore 29 in the tube segment 27; but it may lie at a variety of other angles to the bore 29.

A continuous ridge 46 (See FIG. 3) formed at the bottom of the canister segment 28 proximate the protuberance 38 contacts and cooperates with the tube segment 27 to define the passageway 36. (The continuous ridge 46 may be a portion of the tube segment 27 rather than the canister segment 28.) This ridge 46 prevents the air flowing through the opening 35 from escaping from the casing 21. A flange portion 47 disposed around the periphery of the canister segment 28 at the bottom of the segment provides a further seal for the gas flowing through the opening 35.

Securing means such as sonic welding or adhesive secures the tube segment 27 and the canister segment 28 along the lines of contact provided by the ridge 46 and the flange 47. Alternatively, an annular snap fit design molded into protuberance 38 releasably secures the tube segment 27 to the canister segment 28. In this alternative, the two segments 27 and 28 are not fixedly secured to each other. Thus, a user may remove and dispose the tube segment 27 after one or more uses and replace it with a new one. Also, a rubber gasket 48 disposed between the tube segment 27 and the canister segment 28 provides a further seal around the opening 35. (The gasket 47 includes openings 49 and 50 through which the ridge 46 and the protuberance 38, respectively, extend.) In the construction with tube and canister segments secured together, the pocket between the two segments may or may not include a gasket 48.

A polyester laminate 28a forms a graphic overlay with built-in membrane switches. (See FIG. 4) The graphic overlay provides a clear plastic cover over the Liquid Crystal Display (LCD) to protect it, while holding the components in place with adhesive. The overlay may also contain electrically conductive paths for transmitting data externally and/or supplying power from the battery source P.

Figure 5:
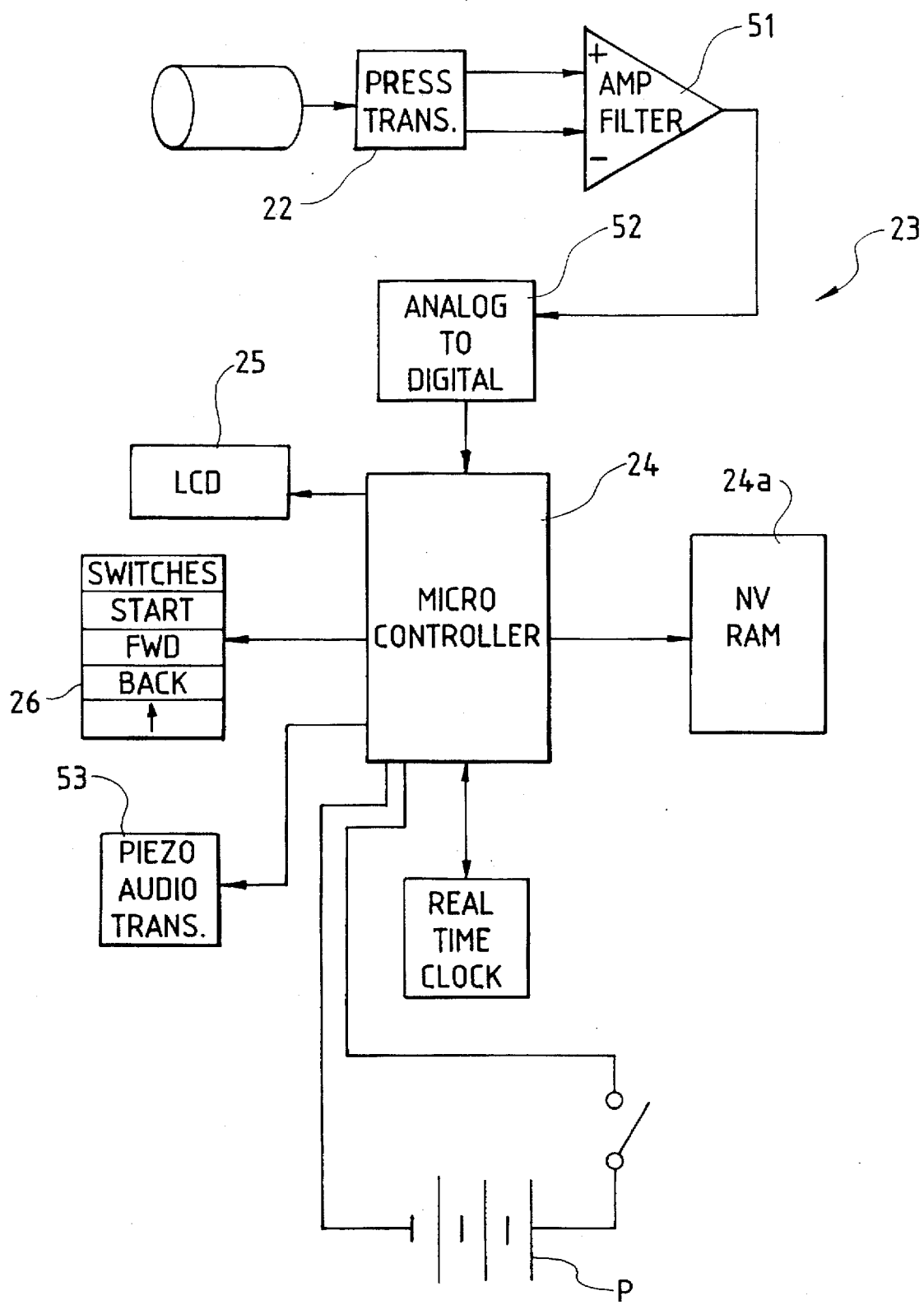

As shown in FIG. 5, the controls 23 amplify an analog signal from the pressure transducer at 51. An analog to digital converter 52 receives the amplified analog signal and converts it. The CPU 24 receives the output of the converter and converts it into a series of flow and time points for each pulmonary test. The NVRAM 24a temporarily stores the data and establishes an optimum scaling factor to provide the best resolution of these data points. It then applies an algorithm, e.g., the cubic algorithm of least squares, to the data to determine the instantaneous flow about a point in time. Then, it transmits the data to the spirometer display 25. (The data may also be transferred electronically to a personal computer or modem through physical contact using a serial interface, or transferred acoustically to a phone through an audio transducer using pulse code modulation.) At a predetermined inspiratory flow, the CPU 24 provides a signal to an audio transducer 53 which provides an audio signal. This audio signal serves as an indication for a subject to activate the medication. When the inspiratory flow drops to a predetermined level, the CPU 24 may provide another signal to the audio transducer 53 as an indication for the subject to begin holding his or her breath. The CPU 24 may then produce another audio signal after a predetermined time period to indicate the end of the procedure.

Figure 6:
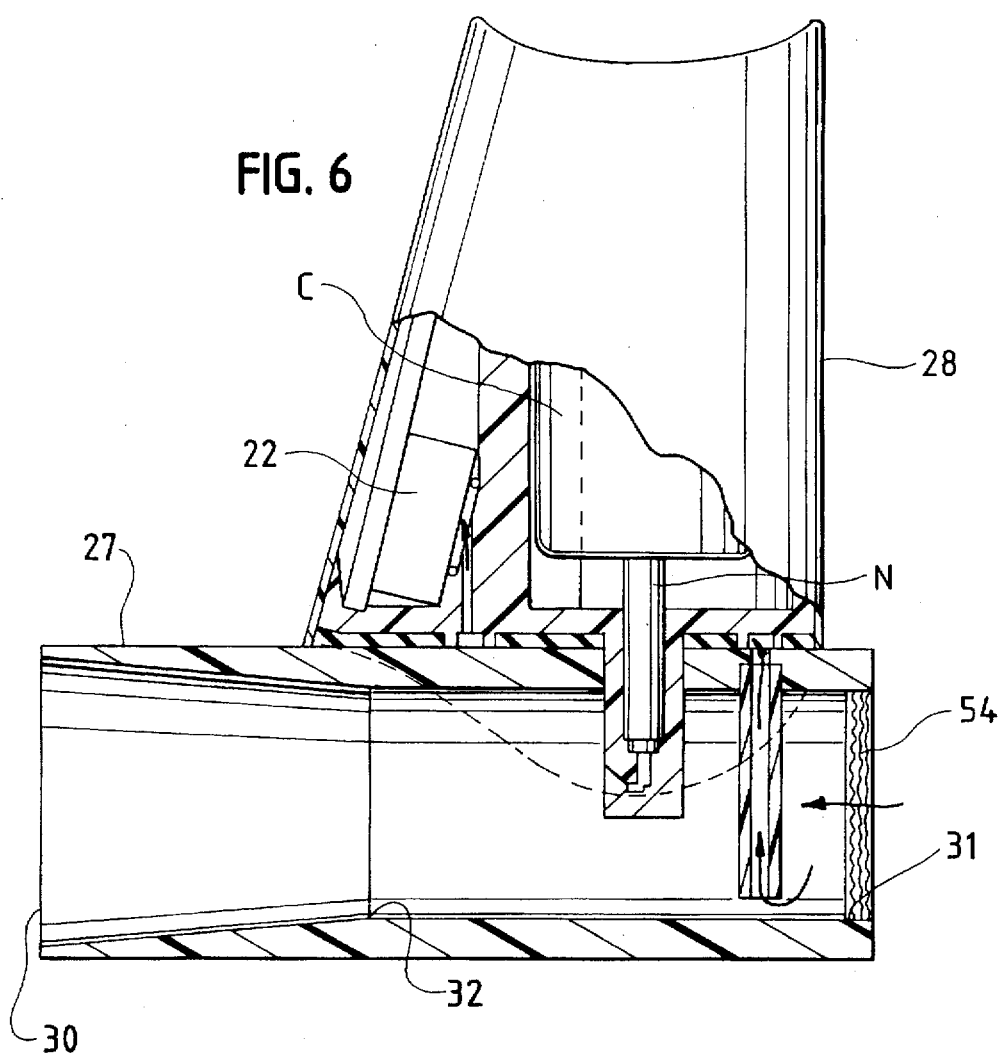

FIG. 6 shows a modification of the casing and spirometer of the present invention. In this modification, the bore between the point 32 and the opening 31 has the same diameter as that of the opening 31. However, this modification includes a fibrous paper or a metal screen 54 at the opening 31 (or at any position within the bore 29) to create the back pressure needed for the pressure transducer 22. It also includes a tube segment 55 that increases the length of the bore 34 and moves the inlet of that bore to the opposite side of the bore 29.

Figure 7:
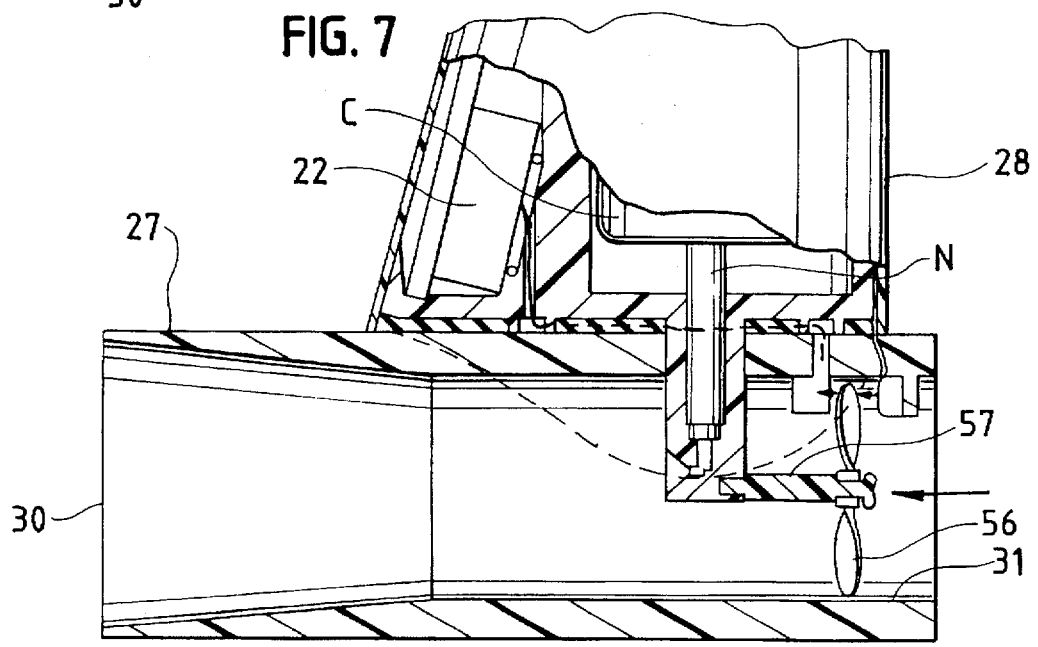

FIG. 7 shows a further modification of the casing and spirometer apparatus of the present invention. This modification also includes an opening 31 that has the same diameter as the diameter of the bore 29 between the point 32 and the opening 31. This modification includes a fan 56 rotatably mounted on a shaft 57 that lies fixedly secured to the protuberance 38. Every time the fan 56 rotates, one of its blades interrupts a beam of light shining on a photocell, producing a pulse of electricity that a digital circuit counts. The faster the air flow, the faster the fan spins and the faster the photocell produces of pulses. This modification may alternatively include an additional photocell or a hall effect sensor to determine the direction of the air flow.

FIGS. 8 through 10 show yet another modification of the casing and spirometer apparatus of the present invention. In this modification, the tube segment 27 includes a cap 58 for the opening 31 and a flap valve 59 for the opening 30. The cap 58 defines openings 60 through which inhaled air may enter the bore 29 at a limited rate to maximize medication efficacy. The flap valve 59 normally closes the bore or cavity 29 but opens under the force of a subject's inhalation. Exhalation will not open the valve in the opposite direction.

Acting as a spacer, this modification allows a subject to close the discharge opening 30 of the tube segment 27 for a short period of time while discharging the medication from the canister C allowing the large droplets in the aerosolized medication to settle to the bottom of the cavity 29. In this way, the subject may only inhale the aerosolized medication and effectively deliver the medication into his or her lungs.

While the above description and the drawings disclose and illustrate one embodiment and a number of modifications of that embodiment, one should understand, of course, that the invention is not limited to this embodiment and modifications. Those skilled in the art to which the invention pertains may make other modifications and other embodiments employing the principles of this invention, particularly upon considering the foregoing teachings. Therefore, by the appended claims, the applicants intend to cover any modifications and other embodiments as incorporate those features which constitute the essential features of this invention.

What is claimed is:

1. An apparatus for dispensing a metered amount of aerosolized medication and for measuring breathing functions of a human subject, said apparatus comprising: a casing defining a cavity, a first opening through which the subject inhales from the cavity or exhales into the cavity, a second opening through which air enters the cavity when the subject inhales or discharges from the cavity when the subject exhales, obstruction means for obstructing the flow through the cavity and developing back pressure in the cavity, and a third opening in fluid communication with the cavity between the first opening and the obstruction means; pressure sensing means in fluid communication with the third opening for sensing, between the first opening and the obstruction means, back pressure of breath moving through the cavity, developed by the obstruction means between the first opening and the obstruction means; said casing also defining an open pocket for receiving a pressurized canister and passageway means including a fourth opening for discharging the contents of the canister from the canister directly into the cavity of the casing; and means for indicating when to activate medication at a predetermined inspiratory flow during an inspiratory procedure.

2. The apparatus of claim 1, further comprising means for receiving an input signal from the pressure sensing means and for providing an output signal characteristic of the pressure of breath moving through the cavity.

3. The apparatus of claim 1, wherein the casing is a generally L-shaped member, the cavity comprises a first bore that extends from the first to the second opening, and the pocket comprises a second bore that extends generally perpendicularly of the first bore.

4. The apparatus of claim 1, wherein the casing includes an elongate tube portion that defines the first bore and the first and second openings, the first opening being disposed at one end of the tube portion and the second opening being disposed at an opposite end of the tube portion.

5. The apparatus of claim 4, wherein the tube portion is round.

6. The apparatus of claim 1, wherein the first opening has a greater cross-sectional area than the cross-sectional area of the second opening and wherein the obstruction means includes a flange portion adjacent the second opening.

7. The apparatus of claim 1, wherein the third opening includes a passageway between the cavity and the pressure sensing means.

8. The apparatus of claim 1, wherein the fourth opening includes a passageway that communicates with the pocket and receives a nozzle of the canister.

9. The apparatus of claim 1, wherein the pressure sensing means includes an electric transducer.

10. The apparatus of claim 1, wherein the obstruction means includes a screen disposed over the second opening for building back pressure in the cavity.

11. The apparatus of claim 1, wherein said apparatus is sized to fit in a palm of a user's hand.

12. The apparatus of claim 2, further comprising means for generating an audio signal at a predetermined level of pressure.

13. An apparatus for dispensing a metered amount of aerosolized medication for a human subject, said apparatus comprising: a casing defining a cavity, a discharge opening through which the subject receives the medication, a valve means for the discharge opening, said valve means opening under force provided by the subject's inhaling, an air opening through which air enters the cavity, and a medication opening through which the aerosolized medication enters the cavity, the casing further defining an open pocket for receiving a pressurized canister and passageway means including the medication opening for allowing medication from the canister to discharge directly into the cavity; and mean for indicating when to activate medication at a predetermined inspiratory flow during an inspiratory procedure; said apparatus being sized to fit into a palm of a user's hand.

14. The apparatus of claim 13, wherein the casing is a generally L-shaped member, the cavity comprises a first bore that extends from the first to the second opening, and the pocket comprises a second bore that extends generally perpendicularly of the first bore.

15. The apparatus of claim 13, wherein the casing includes an elongate tube portion that defines the discharge bore and the discharge or air openings, the discharge opening being disposed at one end of the tube portion and the air opening being disposed at an opposite end of the tube portion.

16. The apparatus of claim 15, wherein the tube portion is round.

17. The apparatus of claim 13, wherein the first opening has a greater cross-sectional area than the cross-sectional area of the second opening.

18. The apparatus of claim 13, wherein the medication opening includes a passageway that communicates with the pocket and receives a nozzle of the canister.

19. In an apparatus for dispensing a metered amount of aerosolized medication, a disposable member defining a cavity, a first opening through which a subject inhales from the cavity or exhales into the cavity, a second opening through which air enters the cavity when the subject inhales or discharges from the cavity when the subject exhales, obstruction means for obstructing flow through the cavity, a third opening between the first opening and the obstruction means for sensing back pressure in the cavity, a fourth opening through which medication discharges into the cavity, said cavity being free of additional obstructions capable of developing additional back pressure between the first opening and the obstruction means to affect the operation of said apparatus, and attaching means for releasably connecting the disposable member to another segment of the apparatus.

20. An apparatus for dispensing a metered amount of aerosolized medication and for measuring breathing functions of a human subject, said apparatus comprising: a first, tube segment for defining a cavity, a first opening through which the subject inhales from the cavity or exhales into the cavity, a second opening through which air enters the cavity or discharges from the cavity, and a third opening, said tube segment including obstruction means for developing back pressure in the cavity; a second, canister segment releasably secured to the tube segment and defining an open pocket for receiving a canister; pressure sensing means in fluid communication with the third opening for sensing the back pressure developed by the obstruction means between the first opening and the obstruction means; said canister segment and said tube segment defining passageway means including a fourth opening for the cavity between the third and first openings, said passageway means directing the contents of the canister directly into the cavity; and means for indicating when to activate medication at a predetermined inspiratory flow during an inspiratory procedure.

21. The apparatus of claim 20 wherein the tube segment is a cylinder and the cavity is a bore through the cylinder with an opening at one end being the first opening and an opening at an opposite end being the second opening, the second opening being smaller than the first, a flange position around the second opening being the obstruction means.

22. The apparatus of claim 20, wherein said apparatus is sized to fit in a palm of a user's hand.

* * * * *

UNITED STATES PATENT AND TRADEMARK OFFICE
CERTIFICATE OF CORRECTION

PATENT NO. : 5,724,986
DATED : March 10, 1998
INVENTOR(S) : William C. Jones, Jr. et al.

It is certified that error appears in the above-indentified patent and that said Letters Patent is hereby corrected as shown below:

On the title page:

delete "[73] Assignee: Jones Medical Instrument Co., Oakbrook, Ill."

Column 6, line 51, delete "mean" and substitute therefor -- means --.

Signed and Sealed this

Thirteenth Day of October 1998

Attest:

BRUCE LEHMAN

*Attesting Officer*  *Commissioner of Patents and Trademarks*